(12) United States Patent
Nozaki et al.

(10) Patent No.: US 6,530,909 B1
(45) Date of Patent: Mar. 11, 2003

(54) URINE ABSORBENT BAG

(75) Inventors: Satoshi Nozaki, Ehime-ken (JP); Takashi Maeno, Ehime-ken (JP); Makoto Utsunomiya, Chiba-ken (JP); Yutaka Sakamoto, Kanagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/468,124

(22) Filed: Dec. 21, 1999

Related U.S. Application Data

(63) Continuation-in-part of application No. 09/031,813, filed on Feb. 27, 1998, now abandoned.

(30) Foreign Application Priority Data

Feb. 27, 1997 (JP) .................................. 9-43552

(51) Int. Cl.$^7$ ................................ A61F 13/15
(52) U.S. Cl. ...................... 604/349; 4/194.3
(58) Field of Search ..................... 604/327, 346, 604/347, 349; 4/144.3

(56) References Cited

U.S. PATENT DOCUMENTS

| | | |
|---|---|---|
| 3,707,969 A * | 1/1973 | Sanford ..................... 128/287 |
| 4,559,051 A | 12/1985 | Hanson |
| 4,627,846 A | 12/1986 | Ternstrom |
| 4,886,509 A | 12/1989 | Mattsson |
| 5,078,707 A | 1/1992 | Klug |
| 5,342,332 A | 8/1994 | Wheeler |
| 5,586,978 A | 12/1996 | Bayne |
| 5,618,279 A * | 4/1997 | Pudlo ...................... 604/385.1 |
| 5,735,837 A * | 4/1998 | Ishikawa ................. 604/385.1 |
| 5,827,250 A | 10/1998 | Fujioka et al. |
| 6,059,762 A * | 5/2000 | Boyer et al. ............... 604/349 |

FOREIGN PATENT DOCUMENTS

| | | |
|---|---|---|
| JP | 61-30653 | 9/1986 |
| WO | WO 88/06008 | 8/1988 |

* cited by examiner

*Primary Examiner*—Aaron J. Lewis
*Assistant Examiner*—Michael Bogart
(74) *Attorney, Agent, or Firm*—Lowe Hauptman Gilman & Berner, LLP

(57) ABSTRACT

A urine absorbent bag includes a pair of pad sections placed one upon another. These pad sections are sealed together along one of the longitudinally opposite ends extending transversely of the bag and along adjacent side edge portions extending longitudinally of the bag and being contiguous to the one end. The pad sections are left unsealed along the other longitudinal end and along the remaining zones of the respective side edges extending adjacent the sealed side edge portions to define foldable regions. A guide structure for insertion of a wearer's penis is formed in one of the foldable regions.

26 Claims, 4 Drawing Sheets

FIG.2
FIG.3
FIG.5
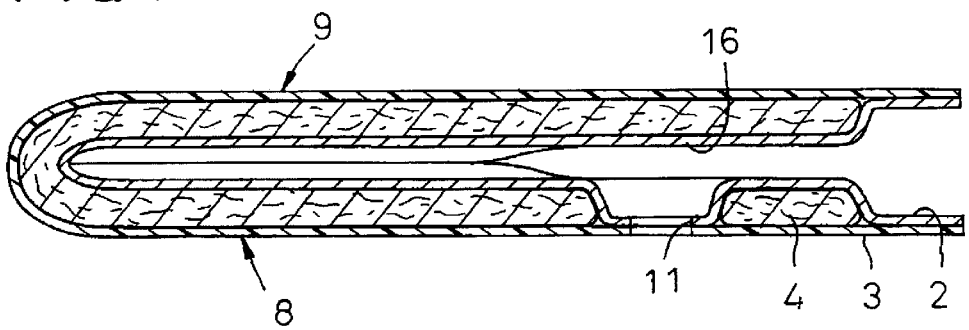
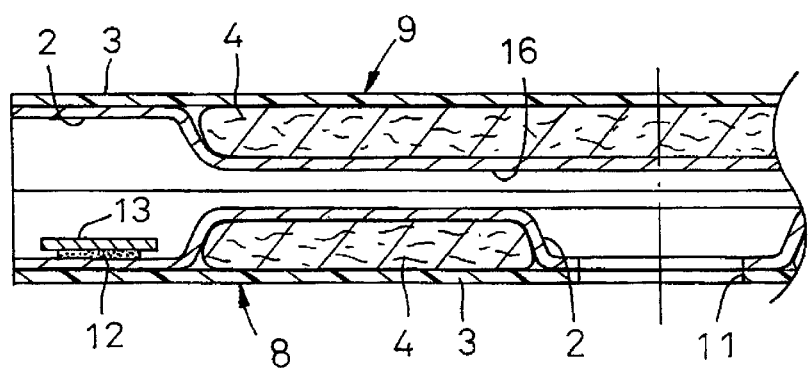
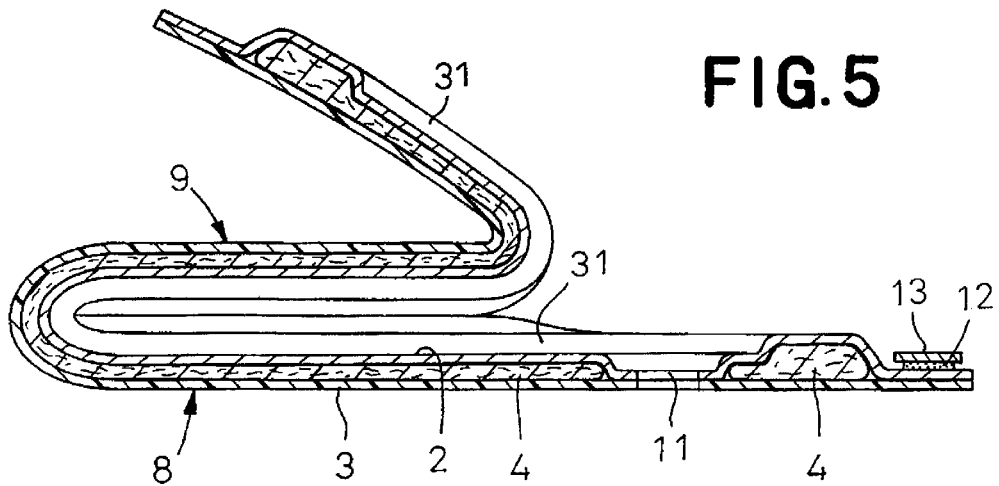

URINE ABSORBENT BAG

The present application is a continuation-in-part of U.S application Ser. No. 09/031,813 filed Feb. 27, 1998, entitled URINE ABSORBENT BAG, now abandoned.

BACKGROUND OF THE INVENTION

This invention relates to urine absorbent bags for bedridden patients and persons suffering from incontinence.

A urine absorbent bag disclosed in Japanese Utility Model Application Publication (Kokoku) No. Sho61-30653 comprises a pair of pads, each including a liquid-permeable topsheet, a liquid-impermeable backsheet and a liquid absorbent core disposed between these two sheets and which are placed one upon another and sealed together along peripheral edges of these two pads to form a bag. One of these pads is formed with a through-hole for insertion of a wearer's penis.

With this prior art urine absorbent bag, the wearer must force his penis into the bag through the hole from an outside thereof and this often makes it difficult to wear the bag smoothly particularly when the wearer is an aged patient. While the through-hole may be dimensioned to be relatively large in order to solve this problem, this inevitably increases concern that the bag might fall off from the wearer's penis.

SUMMARY OF THE INVENTION

In view of the problem as described above, it is a principal object of the invention to provide a urine absorbent bag that is easily worn and substantially free from any apprehension that the bag might fall off from the wearer's penis.

The object set forth above is achieved, according to the invention, by a urine absorbent bag substantially in a rectangular shape formed by a pair of pad sections, each pad comprising a liquid-permeable topsheet, a liquid-impermeable backsheet and a liquid-absorbent core disposed therebetween. The peripheral edges of the respective pads are placed one upon another and partially sealed together so that portions remaining at the peripheral edges are left unsealed so as to form an opening.

Each of the peripheral edges comprises a pair of longitudinally opposite ends extending in parallel to each other transversely of the bag and a pair of transversely opposite side edges extending in parallel to each other longitudinally of the bag. The pad sections placed one upon another are sealed together along one of the longitudinally opposite ends and the transversely opposite side edges extending continuously with and adjacent to the one of longitudinally opposite ends and left unsealed along the other of the longitudinally opposite ends and extents of remaining at the respective side edges so that regions of the respective pad sections defined by the peripheral edges left non-sealed can be folded outwardly of the urine absorbent bag; and one of these foldable regions of the respective pad sections is formed at a location intended to be exposed as the corresponding region of the other pad section is folded outward with guide means extending through a thickness of this region for insertion of a wearer's penis.

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF THE DRAWINGS

FIG. 2 is a sectional view taken along line II—II in FIG. 1, in which upper and lower pads are placed one upon another.

FIG. 3 is a sectional view taken along line III—III in FIG. 1, in which upper and lower pads are placed one upon another.

FIG. 5 is a sectional view taken along line V—V in FIG. 4; and

DESCRIPTION OF THE PREFERRED EMBODIMENTS

Details of a urine absorbent bag according to the invention will be more fully understood from the description given hereunder in reference with the accompanying drawings.

Figure 1:
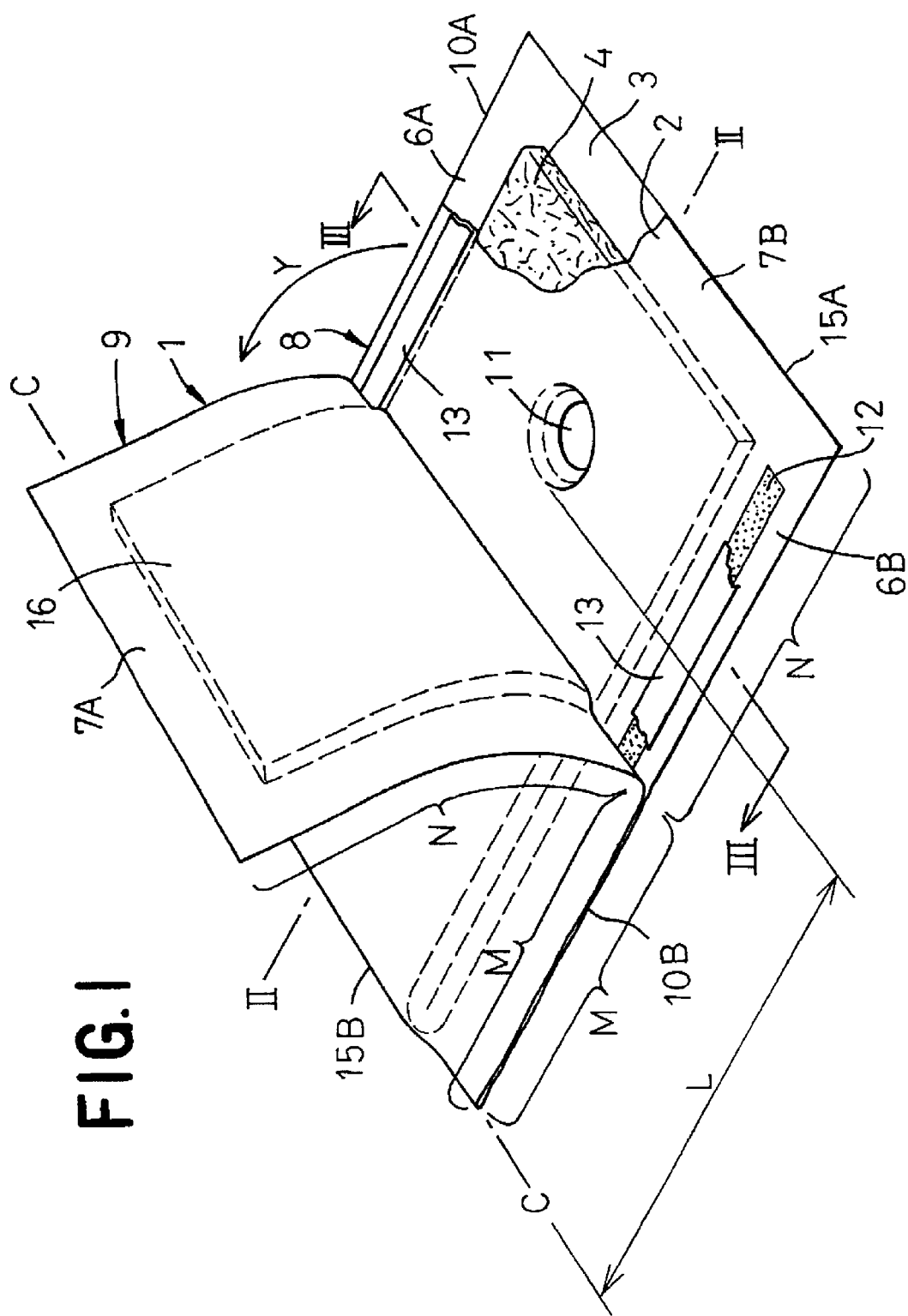
FIG. 1 is a perspective view of an embodiment of a urine absorbent bag according to the invention as partially broken away

The FIG. 1 specific embodiment of the urine absorbent bag is formed by folding a single rectangular pad I comprising a liquid-permeable topsheet 2, a liquid-impermeable backsheet 3 and a liquid-absorbent core 4. The topsheet 2 and the backsheet 3 are placed one upon another and bonded together along portions thereof extending outward beyond a peripheral edge of the absorbent core 4 by—means of hot melt adhesive or heat-sealing effect of at least one of the sheets 2, 3 so as to form a pair of transversely opposite side edges 6A, 6B extending in parallel to each other longitudinally of the pad 1 and a pair of longitudinally opposite ends 7A, 7B extending in parallel to each other transversely of the pad 1. The pad 1 is folded with the topsheet 2 lying inside along a center line C C extending across a full width of the pad 1 in longitudinally lower and upper pad sections 8, 9 which form together a rectangular urine absorbent bag. The urine absorbent bag formed in this manner has one end 15A defined by the pair of longitudinally opposite ends 7A, 7B, the other end 15B extending along the center line C—C in parallel to the one end 15A and a pair of transversely opposite side edges 10A, 10B defined by the side edges 6A, 6B, respectively, extending in parallel to each other.

The lower pad section 8 is formed in a transversely middle region thereof with guide means for insertion of a wearer's penis in the form of a circular hole 11 extending through the pad section 8 in the direction of thickness thereof. The side edges 6A, 6B of the lower pad section 8 are bonded in a water-tight fashion to the side edges 6A, 6B of the upper pad section 9 over a first zone M of the side edges 6A, 6B longitudinally extending from the center line C—C. i.e., the urine absorbent bag is peripherally sealed in this first zone M. Over a second zone N of the side edges 6A, 6B extending between the first zone M and the end 7B, the pair of pads 8, 9 are not peripherally sealed together. Over the second zone N of the side edges 6A, 6B, however, the lower pad section 8 is applied with adhesive agents 12 by means of which the upper pad section 9 can be peripherally bonded to the lower pad section 8 and the adhesive agents 12 are protectively covered with release sheets before the bag is actually used.

Regions of the respective pad sections 8, 9 extending between the second zones N of the side edges 6A, 6B, the pad sections 8, 9 placed one upon another can be folded outward. Regarding the upper pad section 9, a square U-shaped region 16 defined by the second zone N of the respective side edges 6A, 6B and the one end 7A can be folded outward of the bag as indicated by an arrow Y. FIG. 1 shows a state in which the region 16 has been folded outward of the bag and an inner side of the lower pad section 8 is partially exposed. A region of the lower pad section 8 thus exposed is formed with the guide means 11 for insertion of a wearer's penis. FIGS. 2 and 3 show the bag as the region 16 of the upper pad section 9 has been placed upon the lower pad section 8.

A length of the first zone M of the respective side edges 6A, 6B in the lower and upper pad sections 8, 9 extending from the center line C—C toward the ends 7A, 7B is dimensioned to be less than a linear distance L as measured from the center line C—C to a periphery of the guide means 11 for insertion of a wearer's penis in order to assure that the guide means 11 for the insertion is adequately exposed as the region 16 is folded outward of the bag as shown by FIG. 1.

With the urine absorbent bag constructed as has been described above, the wearer may insert his fingers into the guide means 11 from the inner side toward the outer side of the bag to guide his penis from the outer side into the inner side of the bag. The penis once having been guided into the bag may be laid so as to be oriented to the center line C—C or to the side edge 7A or 7B. In any case, after the penis has been laid, the release sheets 13, are peeled off from the adhesive agents 12 and then the region 16 of the upper pad section 9 is placed upon the lower pad section 8 so that these pad sections 8, 9 may be peripherally bonded together.

In the case of this embodiment of the urine absorbent bag, the first zones M of the respective side edges 6A, 6B may be reliably manufacture sealed together (i.e. during manufacturing) to be urine tight. As the terms are used herein, the terms 'permanently sealed together', or 'permanently bonded together', 'permanently sealed edges', and 'manufacture sealed' or 'manufacture sealed edges' are intended to mean that side edges 6A, 6B are sealed together in a urine tight manner during manufacture of the urine absorbent bag in such a manner that the only way in which the sealed edges may be pulled apart from each other will result in physical destruction or tearing of one or both side edges 6A, 6B, meaning that the material forming the side edges, i.e. the topsheet 2, the backsheet 3, or both, will become actually or physically torn in the event that sufficient pressure is applied to pull the sheets apart in the vicinity of the permanent or manufactured seal. The penis may be laid so as to be oriented to the center line C—C to avoid any apprehension that urine leakage might occur due to a defective closure of the bag by a helper or a wearer himself using the adhesive zones. This bag allows for a relatively high freedom of the fingers of a wearer for insertion of this penis. Therefore, fitting of peripheral edge of the guide means 11 around the penis can be improved by appropriately reducing the diameter of the guide means 11 in the form of the circular through-hole without making it significantly difficult to insert the penis into the through-hole. The guide means 11 for insertion of a wearer's penis may be provided along the peripheral edge thereof with an elastic member not only to facilitate insertion of the fingers into the guide means 11 but also to improve the fitting around the penis. In consequence, both leakage of urine from the guide means 11 and falling off of the urine absorbent bag from the penis can be effectively avoided.

Figure 4:
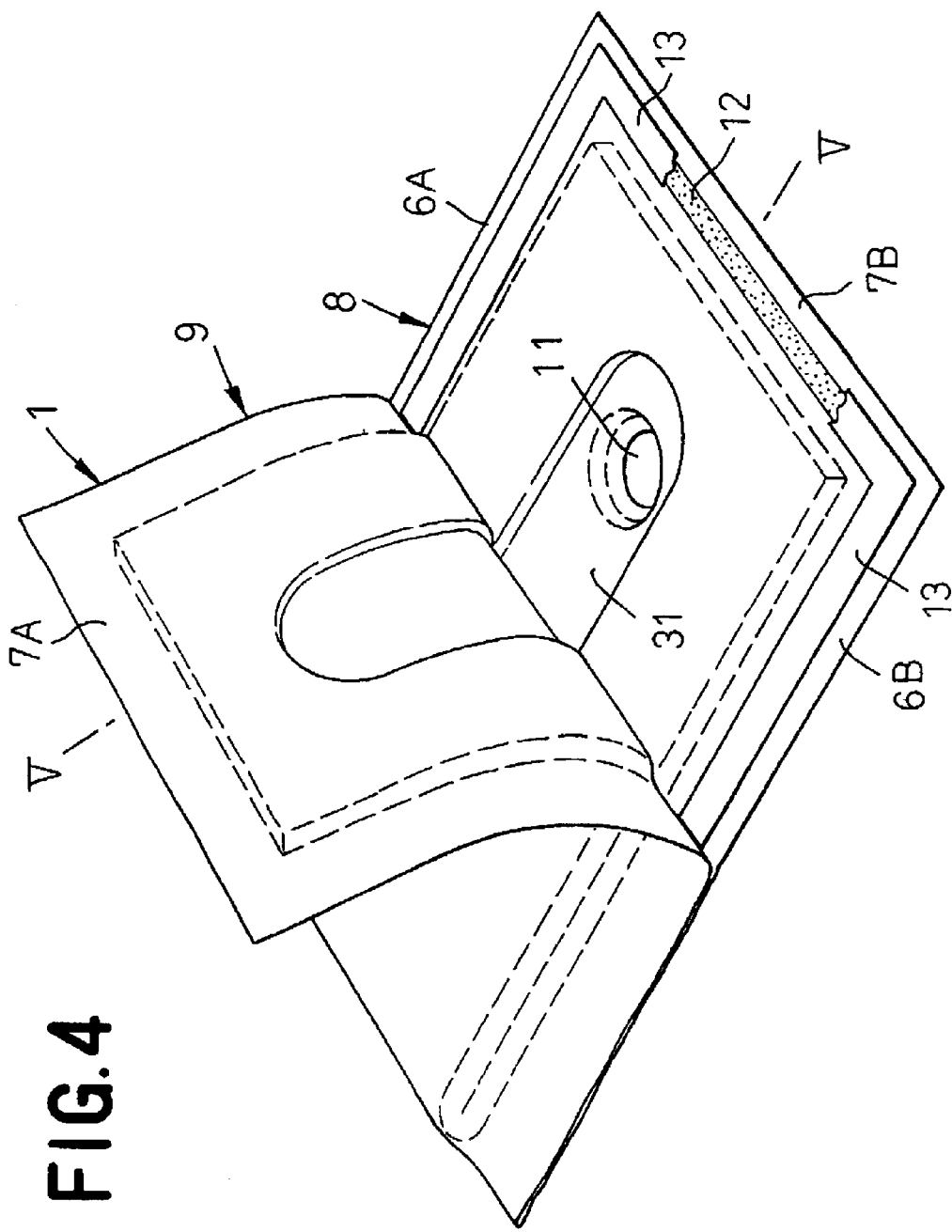
FIG. 4 is a perspective view of another embodiment of the invention.

FIGS. 4 and 5 are respectively a view similar to FIG. 1 and a sectional view taken along a line V—V in FIG. 4 both showing another embodiment of the urine absorbent bag according to the invention. According to this embodiment, the inner side of the urine absorbent bag is formed in a transversely middle region of the lower pad section 8 with a groove 31 extending in parallel to the side edges 6A, 6B.

The groove 31 preferably extends also in the corresponding region of the upper pad section 9. The penis inserted into the bag may be laid within the groove 31 to stabilize position as well as orientation of the penis within the urine absorbent bag. By positioning the penis in the middle region of the bag in this manner, discharged urine more evenly and quickly spreads transversely of the absorbent core 4 and leakage of urine is effectively avoided than the case in which the penis is positioned to one side within the urine absorbent bag. According to this embodiment, the lower pad section 8 is applied along the side edges 6A, 6B and the one end 7B with the adhesive agent 12 so as to describe a square U-shape. The adhesive agent 12 is protectively covered with the release sheet 13 before the bag is actually used.

Figure 6:
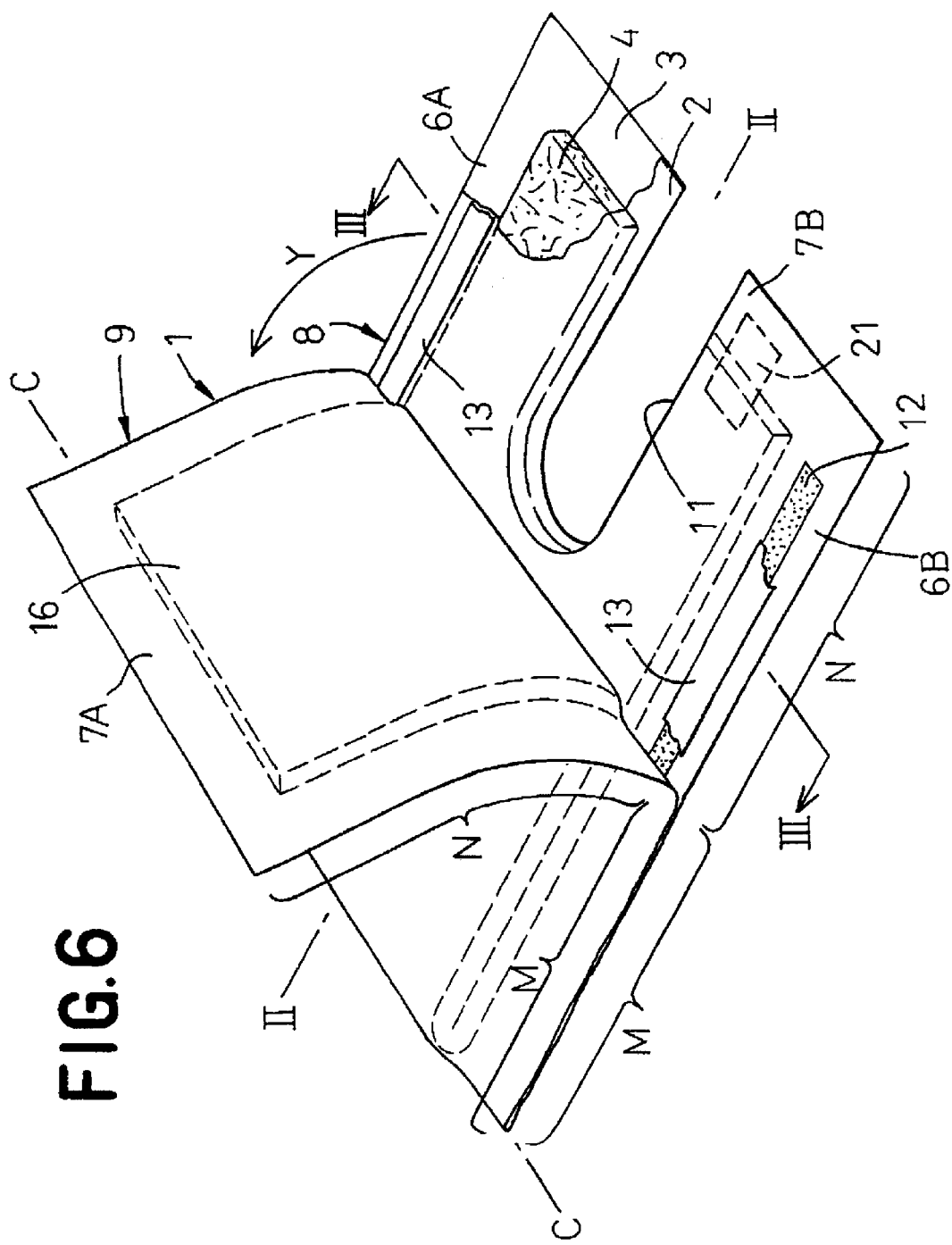
FIG. 6 is a view similar to FIG. 1 of still another embodiment of the invention.

FIG. 6 is a view similar to FIG. 1 showing still another embodiment of the urine absorbent bag. According to this embodiment, the guide means 11 for insertion of a wearer's penis comprises a U-shaped cutout, instead of the circular through-hole, provided in the lower pad section 8. An outer surface of the backsheet 3 is formed in the proximity of the guide means 11 for insertion of a wearer's penis with a fastening zone 21 applied with an adhesive agent so that portions of the lower pad section 8 extending along the U-shaped cutout may be fastened around the proximal end of the penis in order to avoid falling off of the bag from the penis.

It should be understood that the urine absorbent bag may be formed by placing two separate pad members one upon another without departing from the scope of the invention. In this case, a thickness as well as composition of the liquid-absorbent core 4 in one of the pad members 8, 9 can be freely selected independently of the other pad member.

The urine absorbent bag according to the invention comprises the upper and lower pad sections placed one upon another, wherein one of these pad sections is formed with the guide means for insertion of a wearer's penis and the region of the other pad section covering the guide means is foldable outwardly of the bag. The guide means for a wearers insertion of penis is exposed as the region is folded outwardly of the bag. With the wearer's fingers inserted into the guide means from the inner side toward the outer side of the bag, it is easily achieved to guide the penis into the bag.

The guide means for insertion of a wearer's penis in the form of the circular through-hole advantageously makes it easy to fit the peripheral edge of the guide means around the penis.

The guide means for insertion of a wearer's penis in the form of the U-shaped cutout advantageously facilitates insertion of the penis.

The transversely opposite side edges as well as the longitudinally opposite ends of the urine absorbent bag initially in non-sealed state may be applied with adhesive to assure that the bag can be urine-tightly closed after the penis has been inserted into the bag.

The groove formed inside the urine absorbent bag advantageously enables the position and orientation of the penis within the bag to be stabilized.

The urine absorbent bag formed by folding a single pad in two advantageously simplifies manufacturing of the urine absorbent bag in comparison with the case in which a pair of separately prepared pads are placed one upon another to form the urine absorbent bag.

However, the urine absorbent bag formed by placing a pair of separately prepared pads is advantageous in that a thickness as well as a composition of the liquid-absorbent core in each of these two pads can be freely selected independently of the other pad.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

What is claimed is:

1. A urine absorbent bag, comprising a pair of pad sections each including a liquid-permeable topsheet, a liquid-impermeable backsheet and a liquid-absorbent core disposed between said topsheet and backsheet, wherein:

each of the pad sections includes a pair of longitudinally opposite ends extending in parallel to each other transversely of the bag and a pair of transversely spaced opposite side edges extending in parallel to each other longitudinally of the bag;

the pad sections are placed one upon another and are either continuously sealed together or are integrally formed along one of said longitudinally opposite ends;

the transversely opposite side edges of each of the pad sections comprise first and second edge portions contiguous to said one of said longitudinally opposite ends and the other of said longitudinally opposite ends, respectively;

the respective first edge portions of the pad sections are permanently sealed together while the respective second edge portions thereof are unsealed relative to each other so as to form an opening;

the second edge portions and the other of said longitudinally opposite ends of each of the pad sections together define a foldable region being foldable outwardly of the urine absorbent bag; and the foldable region of one of the pad sections is formed with a guide structure at a location exposable as the foldable region of the other pad section is folded outwardly of the bag, said guide structure extending through a thickness of said one of the pad sections for insertion of a wearer's penis.

2. The bag of claim 1, wherein the guide structure for insertion of a wearer's penis is a circular through-hole.

3. The bag of claim 1, wherein the guide structure is a substantially U-shaped cutout.

4. The bag of claim 2, wherein the second edge portions are at least partially applied with an adhesive agent so that the second edge portions can be partially sealed with the adhesive agent after insertion of the penis.

5. The bag of claim 4, wherein said other of the longitudinally opposite ends includes an adhesive agent on an inner surface thereof.

6. The bag of claim 1, wherein said pad section having the guide structure is further formed, on an inner side thereof in a middle zone between the second edge portions, with a groove extending in parallel to the second edge portions and in a thickness direction of said pad section, said guide structure being disposed in said groove.

7. The bag of claim 1, wherein the pad sections placed one upon another are formed by folding a single pad along a center line extending across a full width of the single pad so as to longitudinally divide the single pad in said two pad sections.

8. The bag of claim 1, wherein the pad sections comprise a pair of separately prepared pads placed one upon another.

9. A urine absorbent bag substantially in a rectangular shape formed by a pair of pad sections each comprising a liquid-permeable topsheet, a liquid-impermeable backsheet and a liquid-absorbent core disposed between said topsheet and backsheet, wherein peripheral edges of the respective pad sections placed one upon another are permanently sealed together in part, and portions remaining at the peripheral edges are left non-sealed so as to form an opening;

each of the peripheral edges comprises a pair of longitudinally opposite ends extending in parallel to each other transversely of the bag and a pair of transversely opposite side edges extending in parallel to each other longitudinally of the bag;

the pad sections are placed one upon another and are sealed together continuously along one of the longitudinally opposite ends and respective extents of the transversely opposite side edges extending continuously with and adjacent to the one of the longitudinally opposite ends, while being left non-sealed along the other of the longitudinally opposite ends and extents remaining at the respective side edges so that separatable regions of the respective pad sections defined by the extents of the peripheral edges left non-sealed can be folded outwardly of the urine absorbent bag;

one of the separatable regions of the respective pad sections is formed at a location exposable as the corresponding region of the other pad section is folded outwardly of the bag with a guide structure extending through a thickness of said one of said separatable regions for insertion of a wearer's penis; and the extents of the transversely opposite side edges in the separatable regions are applied with an adhesive agent so that the extents of the transversely opposite side edges in the separatable regions can be separatably sealed by means of the adhesive agent after insertion of the penis, and the adhesive agent is protectively covered with a release sheet.

10. The bag of claim 9, wherein the guide structure is formed as a circular through-hole.

11. The bag of claim 9, wherein the guide structure is formed as a substantially U-shaped cutout.

12. The bag of claim 11, wherein an inner surface of the other of the longitudinally opposite ends of the urine absorbent bag is also applied with adhesive.

13. The bag of claim 9, wherein, said pad section having the guide structure is further formed on an inner side thereof in a middle zone, which is located between the transversely opposite side edges and includes the guide structure, with a groove extending in parallel to the transversely opposite side edges and in a thickness direction of said pad section.

14. The bag of claim 9, wherein the pad sections placed one upon another are formed by folding a single rectangular pad along a center line extending across a full width of the single pad so as to longitudinally divide the single pad in said two pad sections.

15. The bag of claim 9, wherein the pad sections comprise a pair of separately prepared pads placed one upon another.

16. A urine absorbent bag, comprising first and second pad sections each including a liquid-permeable topsheet, a liquid-impermeable backsheet and a liquid-absorbent core disposed between said topsheet and backsheet, wherein:

each of the pad sections comprise first and second peripheral edge portions which are contiguous and together define an entire boundary of said pad section;

the first peripheral edge portions of the pad sections are placed one upon another and are permanently sealed together;

the second peripheral edge portions of the pad sections are left unsealed relative to each other so as to form an opening;

the second peripheral edge portion of each of the pad sections defines a foldable region being foldable outwardly of said bag;

the foldable region of the first pad section is formed with a guide structure at a location exposable as the foldable region of the second pad section is folded outwardly of said bag; and said guide structure extends through an entire thickness of the first pad sections, and is sized for allowing insertion of a wearer's penis.

17. The bag of claim 16, wherein the guide structure is a through-hole which extends continuously circumferentially for full 360°.

18. The bag of claim 16, wherein the guide structure is a substantially U-shaped cutout.

19. The bag of claim 16, wherein the second peripheral edge portions are at least partially applied with an adhesive agent so that the second peripheral edge portions can be at least partially sealed with the adhesive agent after insertion of the penis.

20. The bag of claim 17, wherein the second peripheral edge portions are fully applied with an adhesive agent so that the second peripheral edge portions can be completely sealed with the adhesive agent after insertion of the penis, so that said bag can be urine-tightly closed along the entire boundary of the pad sections.

21. The bag of claim 17, wherein the foldable region of the first pad section is further formed with a first groove extending in a thickness direction of the first pad section, said guide structure being disposed in said first groove.

22. The bag of claim 21, wherein the foldable region of the second pad section is formed with a second groove at a location corresponding to the first groove, said second groove extending in a thickness direction of the second pad section.

23. The bag of claim 16, wherein the first peripheral edge portions of the pad sections are permanently sealed together in one segment and are formed integrally in another segment so that said bag is urine-tight along the entire first peripheral edge portions.

24. The bag of claim 16, wherein the first and second pad sections are separate elements and the first peripheral edge portions of the pad sections are permanently sealed together so that said bag is urine-tight along the entire first peripheral edge portions.

25. The bag of claim 17, further comprises an elastic element extending circumferentially of the hole.

26. The bag of claim 16, further comprising at least one fastening element positioned on an outer surface of the backsheet of the first pad section.

\* \* \* \* \*